United States Patent [19]
Greenshields

[11] Patent Number: 5,968,811
[45] Date of Patent: *Oct. 19, 1999

[54] PROCESSING OF YEAST REFUSE AND RESULTING PRODUCT

[75] Inventor: Roderick Greenshields, West Glamorgan, United Kingdom

[73] Assignee: CPC International Inc., Englewood Cliffs, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/484,691

[22] Filed: Jun. 7, 1995

Related U.S. Application Data

[63] Continuation of application No. 08/039,415, filed as application No. PCT/GB91/01819, Oct. 17, 1991, abandoned.

[30] Foreign Application Priority Data

Oct. 17, 1990 [GB] United Kingdom .................... 9022560

[51] Int. Cl.$^6$ .............................. C12N 1/14; C12P 19/04; C08B 37/00
[52] U.S. Cl. .................. 435/255.2; 435/100; 435/254.2; 435/255.1; 435/101; 536/123.12
[58] Field of Search ................................ 435/255.2, 100, 435/255.1, 101, 254.2; 536/123.12

[56] References Cited

U.S. PATENT DOCUMENTS

| | | | |
|---|---|---|---|
| 3,975,553 | 8/1976 | Griffon | 426/656 |
| 4,122,196 | 10/1978 | Robbins et al. | 426/60 |
| 4,252,836 | 2/1981 | Akin et al. | 426/602 |
| 4,303,680 | 12/1981 | Tanekawa et al. | 426/60 |
| 4,765,992 | 8/1988 | Geneix et al. | 426/15 |
| 4,810,646 | 3/1989 | Jamas et al. | 434/101 |
| 4,962,094 | 10/1990 | Jamas et al. | 514/54 |
| 4,992,540 | 2/1991 | Jamas et al. | 536/123 |
| 5,037,972 | 8/1991 | Jamas et al. | 536/114 |

FOREIGN PATENT DOCUMENTS

| | | | |
|---|---|---|---|
| 453316 | 10/1991 | European Pat. Off. | B01J 13/02 |
| 460945 | 12/1991 | European Pat. Off. | B01J 13/02 |
| 1144876 | 3/1969 | United Kingdom | C12C 11/34 |
| 920660 | 4/1992 | WIPO . | |

OTHER PUBLICATIONS

Bacon et al, Biochem. J., 114:557–567 (1969).
Moland et al, J. Cell Biology, 85:199–212 (1980).
Fleet et al, J. Gen. Micro., 94:180–192 (1976).
Marconi et al, Int. J. Immunopharm., 4(4):281 (1982).
Microbiologica vol. 6, No. 3, Jul. 1983, Bologna, pp. 207–220: Cassone, A. "Suppression of friend leukemia cell–induced tumours by cellular preparations of candida albicans".
Starke, vol. 37, No. 6, Jun. 1985, Weinheim, Deutschland, pp. 209–211; P. Seethanathan & Li Fu Chen: Modified cellulose products by bleaching and its uses—a preliminary study.

*Primary Examiner*—Francisco Prats
*Attorney, Agent, or Firm*—Norris, McLaughlin & Marcus

[57] ABSTRACT

Yeast refuse having a solids content not exceeding 20% by weight is digested with a food grade alkaline salt such as sodium bicarbonate, whole cells are separated from the extracted refuse so as to produce a material rich in disrupted cell walls which is then treated with an alkaline extraction agent and bleached either before or after the separation step, followed by lowering the pH of said bleached material using a food grade acid such as dilute hydrochloric acid. The product comprises a yeast beta-glucan which is substantially free of yeast cells, and which predominantly comprises a multiplicity of yeast ghosts or shells comprising substantially uncollapsed yeast cell walls. The yeast ghosts or shells contain a substantially lower quantity of yeast cell contents relative to the whole cells of the yeast refuse.

7 Claims, 5 Drawing Sheets

PROCESSING OF YEAST REFUSE AND RESULTING PRODUCT

This application is a continuation of application Ser. No. 08/039,415, filed Jun. 14, 1993, now abandoned which is a 371 of PCT/G391/01819, filed Oct. 17, 1991.

The present invention is concerned with processing of waste from a yeast extraction process, and a product thus obtained.

Yeast extract is commercially produced on a large scale by lysis (e.g. hydrolysis, autolysis or plasmolysis) of baker's yeast or brewer's yeast in suitable form or of other fermentation yeasts (e.g. from gasohol production), which results in soluble material and material which is rich in virtually intact cell wall bodies. The latter material is normally removed from the soluble material by centrifugation. The lysis inevitably results in some disruption of the cell walls, such that there is a substantial proportion of virtually intact cell wall bodies, with at least one zone of discontinuity in the cell wall surface region (that is, holes have resulted in the relevant cell walls). The material containing cell wall bodies (known as yeast refuse, or ref), which has a dark brown colour, an unpleasant odour and rapidly putrefies, contains a number of undesirable materials, such as trace elements, colouring agents, hop extracts, tartrates, microorganisms, bacteria, protein slime and a large amount of insoluble components such as yeast cell wall bodies, as well as a certain amount of unlysed whole cells; such yeast refuse is normally discarded. The soluble material from which the refuse has been separated is normally used for the extraction of useful materials, such as yeast extract.

We have now developed a process of treating yeast refuse which produces a purified form of yeast ghosts or shells having substantially intact cell walls (that is, retaining the in vivo morphology of yeast cell walls in yeast refuse), but without the yeast cell contents. That is, the yeast ghosts correspond in morphology to that of lysed material (the yeast refuse, or ref) and not that of the whole yeast cells; the yeast ghosts comprise essentially yeast beta-glucan.

Yeast beta-glucans are, of course, well known; for example, U.S. Pat. No. 4,810,646 discloses a method of producing yeast beta-glucans, which comprises separating growing Saachromyces cerevisiae yeast from its growth medium, subjecting the intact whole yeast cells to alkaline digestion to solubilise the protein portion of the cell, and treating the insoluble glucan with acetic acid to alter the beta (1–6) linkages. The resulting whole glucan particles are described in U.S. Pat. No. 4,962,094 as being suitable for use as dietary additives and are said to substantially retain the in vivo glucan three dimensional molecular structure of the yeast cells from which they are derived. The cell walls are effectively destroyed in the method described; according to the invention the resulting yeast ghosts or shells are obtained from yeast refuse without destruction of the cell wall structure.

According to one aspect therefore, the present invention provides a process of treating yeast refuse having a solids content not exceeding 20% by weight, which comprises:
(a) extracting said refuse with a food grade alkaline salt;
(b) separating whole cells from the extracted refuse so as to leave a material rich in disrupted but otherwise intact cell walls;
(c) treatment of the latter material with an alkaline extraction agent;
(d) bleaching said material with a bleaching agent or food grade oxidising/reducing agent (such as ascorbic acid) either before or after said separation step; and
(e) lowering the pH of said bleached material using a food grade acid (such as citric acid, orthophosphoric acid, dilute hydrochloric acid or dilute sulphuric acid).

Typical food grade alkaline salts for use in step (a) include sodium, calcium or potassium bicarbonate, or sodium, calcium or potassium carbonate; sodium bicarbonate is most preferred. The yeast refuse typically has a solids content of about 2 to 12%, such as 4 to 8% (generally about 5%) by weight and a viscosity in the range of about 5–15 cP (5% aqueous suspension). The refuse is generally extracted in step (a) of the process according to the invention with the alkaline salt, generally at substantially ambient temperatures for approximately one hour. The alkaline salt (which, as previously mentioned, is preferably sodium bicarbonate) is preferably used in an amount of up to 2.5% (preferably about 1%) weight, based on the total volume of yeast refuse (liquids and solids) and preferably such that the resulting extracted mix has a pH in the range 8 to 12, more preferably about 8 to 9.

The separation of whole cells from the extracted refuse so as to produce material rich in disrupted cell walls is generally carried out by mechanical methods, of which centrifugation is preferred. The centrifuge is typically operated at about 5,000 rpm for differential centrifugation or about 2,500 rpm for static centrifugation. The use of a bicarbonate in stage (a) has been found to assist the separation stage (possibly because of gas evolution which serves to make the yeast cell ghosts lighter).

Following separation, the material is treated with an alkaline extraction and extraction agent such as potassium hydroxide, sodium hydroxide or calcium hydroxide. This treatment with an alkaline extraction agent (which is similar to the process known as mercerisation) typically involves treatment in an alkaline solution having a pH of 8 to 14, preferably about 12 to 12.5. The treatment assists in removing coloured products, dissolving unwanted materials such as protein, opening up the structure of the cell walls and facilitating the bleaching step. The mixture is then preferably heated to a temperature in the range of about 65 to 85° C. for at least one hour. If the final product is required to have a pale cream colour, it is preferred that the alkali used comprises potassium or sodium hydroxide; however if the final product is required to have a white colour it is preferred that the alkali used comprises calcium hydroxide.

The bleaching stage is preferably carried out using hydrogen peroxide or a food-grade oxidising/reducing agent (such as ascorbic acid) when the product is to be used for food purposes; the bleaching is preferably carried out such that the bleached material is pale cream or white in colour, which is advantageous when the resulting product is intended for use as a food grade material such as functional fibre. The bleaching stage is preferably carried out in a reactor and the quantity of material rich in disrupted cell walls introduced into the reactor is preferably monitored such that the material occupies not more than about half of the reactor volume. This is because the bleaching stage typically involves foaming which causes a substantial increase in the volume of the material being treated. Preferably the foaming is substantially controlled using a foam-breaking paddle and can be substantially lessened by the addition of anti-foaming agents.

If the final product is required for use as a food thickener, the bleached material is preferably contacted with a phosphate/citrate buffer having a pH of about 5 to 6 and treated with a yeast-lytic enzyme such as Novozym 234 (which has beta-glucanase side activity) for about 6 hours at a temperature in the range of about 55 to 75° C. The reaction conditions are chosen as described above so as to enhance the endo-beta glucanase activity and substantially inhibit the exo-beta glucanase activity of the Novozym 234. The greater the extent of endo-beta-glucanase treatment, the poorer are the lipomimetic properties, and the greater are the gum properties of the product. The enzyme-treated material is then heated typically to about 70 to 90° C. for at least 30 minutes, centrifuged, resuspended and preferably subjected to further centrifugation prior to drying.

Optionally, the bleached material may be treated with a food grade acid (typically hydrochloric or orthophosphoric acid), centrifuged and treated with lecithin (provided the final product is not required to be used as a thickener). The material may then be further centrifuged prior to drying. Treatment of the bleached material with lecithin is advantageous because lecithin helps to mask any residual flavour or odour pertaining to the yeast refuse.

The lowering of the pH with the food grade acid may be carried out by washing the material being centrifuged, or may be carried out subsequently. The pH is generally lowered to a pH of 5 to 6, either in a single stage, or by lowering initially to a value from about 6 to 7.5 (such as about 7.0) and at a later stage to pH about 5 to 6.

There is further provided by the present invention a product which comprises a yeast beta-glucan which is substantially free of whole yeast cells and which predominantly comprises a multiplicity of yeast ghosts or shells comprising substantially uncollapsed yeast cell walls, said yeast ghosts or shells containing a substantially lower quantity of yeast cell contents relative to the whole cells of said yeast refuse.

Typically the individual yeast ghosts have a maximum dimension in the range of 5 to 20 microns having substantially the same shape and size as the original cells.

The resulting product is further characterised by its stability, as compared to the starting yeast refuse (which readily putrefies), such improved stability being an advantage when the material is required for a comestible product. The present invention therefore further comprises a storage-stable comestible product, which comprises a pale cream or white coloured yeast beta-glucan which is substantially free of whole yeast cells; the product, which comprises physiologically functional fibre, may be in viscous, semi-solid form or it may be dried (typically by freeze drying or spray-drying) to a powdered material. The comestible product is, in a preferred embodiment of the invention, lipomimetic and may be used as such as a fat substitute or may be used together with further food ingredients. In some embodiments, the comestible product may be further processed to produce a material in the nature of a gum or thickener, which typically has a viscosity of the order of at least 300 cP (5% aqueous suspension).

In some embodiments, the product is eminently suitable for use as a biologically acceptable carrier. In particular, the yeast ghosts or shells can provide a transfer medium which enables beneficial substances (such as pharmaceutical or pharmacological preparations or a food source) to be administered to an animal patient.

The product obtained by the process according to the invention may be used for purposes other than foods, and if this is the case, it may be further purified by, for example, solvent extraction using acetone or the like. The product may also be subjected to further bleaching using hydroxide or a bleaching agent such as a hypochlorite whereby a white product may be obtained. The product obtained can be used in topical (skin treatment) formulations, which may be either cosmetic or pharmacologically active.

The present invention therefore further comprises a topical formulation, which comprises a yeast beta-glucan which is substantially free of yeast whole cells, optionally together with one or more topically acceptable ingredients (such as vitamins, perfumes, amino acids, medicaments or the like).

A preferred embodiment of the present invention will now be described with reference to the accompanying drawings:

BRIEF DESCRIPTION OF THE DRAWINGS

Referring to FIG. 1, brewer's yeast A is optionally debittered B and optionally mixed with other yeasts C,D before being passed to a lysis stage for breaking of the cell membranes. The lysis stage may, in the illustrated embodiment, be autolysis E (careful thermal treatment so as to kill the cells without inactivating osmotic equilibrium between the cell contents and their surroundings by the use of a solute such as sodium chloride outside the cell walls), be plasmolysis F or hydrolysis G (using typically an acid such as hydrochloric acid). The lysed product is then separated, typically in a centrifugal separator H. The fraction J containing cell bodies is yeast refuse (or ref), the starting material for the process according to the invention; the remaining material K passes on to be processed to yeast extract by conventional techniques. The yeast refuse typically has a viscosity in the range of about 5 to 15 cP (5% aqueous suspension).

Referring to FIG. 2, yeast refuse J (typically having a solids content of about 5 % by weight) from a yeast extract process X is treated with sodium bicarbonate (typically in an amount of about 1 % by weight, based on the volume of the ref, such that the mix has a pH of about 8.0 to 9). The mix is then stirred in stirring stage L, typically for about one hour at room temperature, and subjected to a separation stage M typically involving alkaline treatment and extraction (mercerisation) using an alkaline extraction agent such as potassium hydroxide. The separation stage results in two streams, disrupted cell walls N and undegraded cells P. The disrupted cell walls N are then treated with a bleaching agent or food grade oxidising or reducing agent in bleaching stage Q. A preferred bleaching agent is hydrogen peroxide or food-grade oxidising/reducing agent such as ascorbic acid (although for some non-food end uses the bleaching agent may be hypochlorite or the like).

Figure 1:
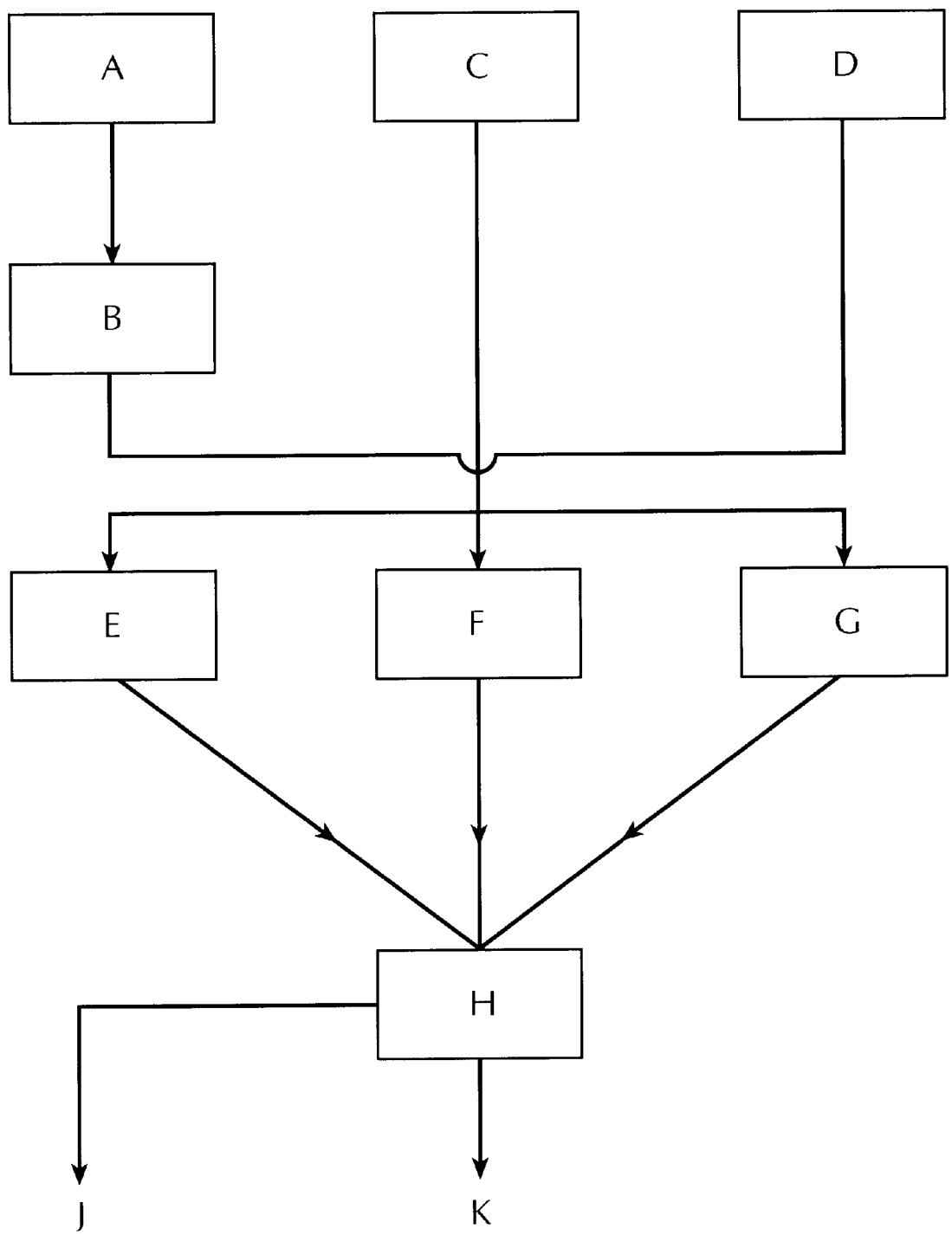
FIG. 1 is a flow chart showing the initial stages of a conventional process for producing yeast extract showing the stage at which there is produced yeast refuse (the starting material in the process according to the invention)
Figure 2:
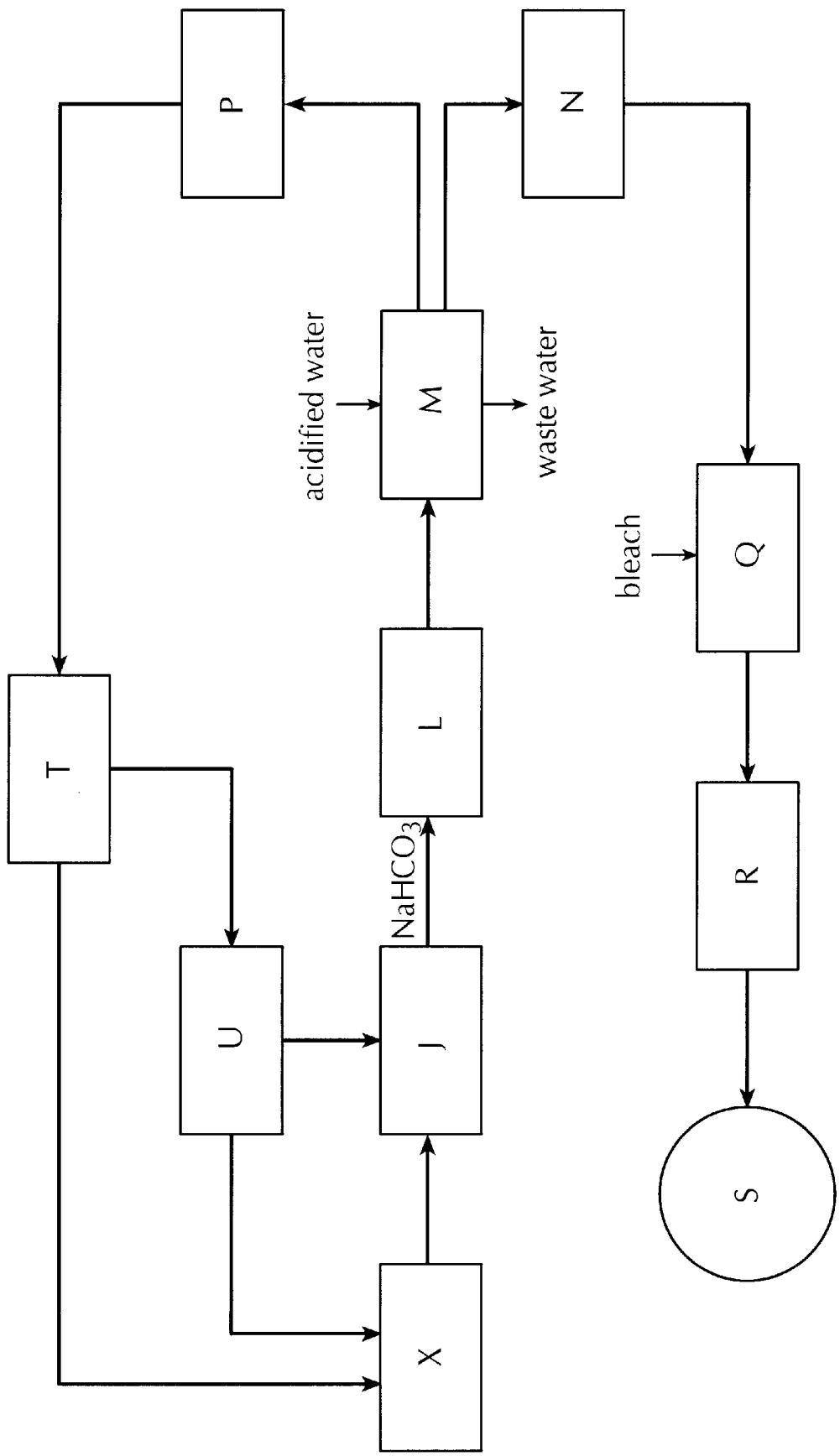
FIG. 2 is a further flow chart schematically illustrating an exemplary embodiment of the process according to the invention.

Bleaching stage Q preferably involves controlled foaming using a foam breaking paddle. Foaming can occupy a further 60% of the reaction volume, but may be reduced with anti-foaming agents. The bleached material is then treated with a phosphate/citrate buffer, and the pH of the mixture is adjusted to approximately 5.5. The bleached cell walls were then heated to about 65° C. and treated with a yeast lytic enzyme (typically Novo 234 beta-glucanase) for about 6 hours. The enzyme-treated material is then placed in a reaction vessel and indirectly heated using either a water bath or a water jacket to a temperature of about 80OC for at least 30 minutes. The material is then further centrifuged, resuspended and then finally centrifuged in stage R. The resulting composition is a food-grade functional fibre material S, which may be used as such, or dried (typically by spray- or freeze-drying) to produce a powder. The resulting dried material can be reconstituted with water to form a material having substantially the same properties as it had prior to drying.

According to a second embodiment of the present invention, separation stage M involves centrifugation in a centrifugal separator (typically at about 2500 rpm for about 10 minutes for static centrifugation or 5,000 rpm for differential centrifugation), in which the mix is washed with water. The centrifuged material results in two streams, cell walls N and undegraded cells P. The cell walls N are resuspended in a dilute solution of an alkaline reagent such as 0.5–5% w/v sodium or potassium hydroxide (to produce a cream product), or calcium hydroxide (to produce a white product) and then adjusted with a 40% sodium or potassium hydroxide such that the pH of cell walls N is in the range of 12 to 12.5. Cell walls N are then indirectly heated (as described above) to at least 70° C. for about 1 hour before being passed to bleaching stage Q, where the material is mixed for about one hour and again heated to at least 70° C. while being treated with bleach. The bleach is preferably hydrogen peroxide or food grade oxidising/reducing agent (although for some non-food end-uses the bleach may be a hypochlorite or the like). Concentrated hydrochloric acid is then added to the bleached material so as to achieve a pH of substantial neutrality and the material is then centrifuged at R. Stage R further comprises resuspension of the bleached material in a suspension medium comprising water and lecithin, further centrifugation and further lowering of the pH to about pH 5.0. The resulting composition is a food-grade functional fibre material S, which may be used as such, or dried (typically by spray or freeze drying) to produce a powder. The resulting dried material can be reconstituted with water to form a material having substantially the same properties as it had prior to drying.

The undegraded cells are digested with a yeast-lytic enzyme (such as Novo 234 beta-glucanase) in digestion phase T (typically with treatment at about 30° C. for about 30 minutes). The enzyme-digested material is then passed to centrifuging stage U, from which is produced a predominantly liquid phase, which is passed to extract stage X, and a predominantly solid phase, which is mixed with the remainder of the yeast refuse J.

Figure 3:
FIG. 3 shows a micrograph of a product according to the present invention taken by confocal microscopy.

Referring to FIG. 3, the yeast beta-glucan shown in the micrograph is substantially free of whole yeast cells and predominantly comprises a multiplicity of yeast ghosts or shells. The yeast ghosts or shells comprise yeast cell walls which have remained substantially intact and contain a substantially lower quantity of cell material than was originally present in the whole cells of the yeast refuse.

Figure 4:
FIG. 4 shows a comparative micrograph of beta-glucan taken by confocal microscopy.

FIG. 4 (which is for comparative purposes only) shows beta-glucan particles produced by a method according to U.S. Pat. No. 4,810,646. The glucan particles comprise whole beta glucan particles aggregated together. The glucan particles shown are clearly different from the yeast ghosts or shells as illustrated by FIG. 3.

Figure 5:
FIG. 5 shows a micrograph illustrating a product according to the present invention and also whole beta-glucan particles, as taken by confocal microscopy.

Referring to FIG. 5, there are shown yeast beta-glucan ghosts or shells according to the present invention, and (at the foot of the micrograph, in the centre) aggregated whole beta-glucan particles produced by a method according to U.S. Pat. No. 4,810,646. As shown in FIG. 5, the yeast beta-glucan ghosts or shells are substantially larger than the individual aggregated beta-glucan particles.

The present invention will now be further illustrated by the following examples which do not limit the scope of the invention in any way.

EXAMPLE 1

Brewer's yeast was subjected to autolysis, for breaking up of the cell membranes. The lysed product was then separated by centrifugation to produce yeast refuse the fraction containing the cell bodies having a viscosity of 10 cP (5% aqueous suspension).

The yeast refuse was then treated with sodium bicarbonate so as to produce an extracted mix having a pH of 8.5. The mix was then stirred for about one hour at room temperature, and centrifuged for further separation.

The centrifuged material resulted in two streams, namely cell wall rich material and undegraded cells. The cell wall rich material was resuspended in 2.5 % sodium hydroxide and then 40% sodium hydroxide added so as to adjust the pH of the material to 12.5. The cell wall rich material was then indirectly heated on a water bath to about 65° C. for about 1 hour and then bleached by treatment with hydrogen peroxide, for about one hour with mixing. Concentrated hydrochloric acid was then added to the bleached material so as to achieve a pH of 7.0; the material was further centrifuged and the pH further lowered to 5.0.

The resulting product (product A) was substantially free of any whole yeast cells and predominantly comprised yeast ghosts or shells having substantially uncollapsed walls. The yeast ghosts contained a lower quantity of yeast cell contents relative to the whole cells of the refuse and were suitable for use in cosmetic formulations (as exemplified in Example 2), pharmaceutical formulations (as exemplified in Example 3), cleaning reagents (as exemplified in Example 4), comestible preparations (as exemplified in Example 5), or to be used as transfer media for pesticides (as exemplified in Example 6).

EXAMPLE 2

The following is a topical formulation suitable for use as a cosmetic cream:

| Components | % Concentration (w/v) |
| --- | --- |
| Product A | 10% |
| Boric acid | 10% |
| Glycerine | 14% |
| Expressed oil of almond | 5% |
| Glyconine | 5% |
| Oil of lavender | 0.05% |

Distilled water can be added to the above mixture as required.

EXAMPLE 3

The following formulation is suitable for use as a pharmaceutical composition which is for topical application:

| Components | % Concentration (w/v) |
|---|---|
| Product A | 10% |
| Phenoxyethanol Emulsifying base) | 1% |
| Hydrocortisone acetate | 0.1–2.5% |
| Chlorocresol (in emulsifying base) | 0.1% |

Distilled water may be added as required to the emulsifying base (in this case phenoxyethanol) which typically contains trace quantities (1–2ppm) of methyl-p-hydroxybenzoate.

EXAMPLE 4

The following is a formulation suitable for use as a household disinfectant:

| Components | % Concentration (w/v) |
|---|---|
| High boiling tar acids (boiling range 220° C.–325°) | 40% |
| Product A | 5–8% |
| 50% Sulphonated castor oil | 0–4% |

Water can be added to the above mixture as required.

EXAMPLE 5

The following formulation is suitable for use as a comestible product, wherein the product according to the present invention is present as a carrier for the flavouring:

| Components | % Concentration (w/v) |
|---|---|
| Product A | 98.45% |
| Cheese Oil | 1% |
| Salt | 0.5% |
| Lecithin | 0.05% |

Lecithin is included in the formulation to help mask any residual flavour or odour pertaining to the yeast refuse.

Potable water can be added to the above mixture as required.

EXAMPLE 6

The following is a formulation suitable for use as a transfer medium which can allow the slow release of pesticides therefrom:

| Components | % Concentration (w/v) |
|---|---|
| Product A | 2–4% |
| Lecithin | 0.1 |
| Pyrethrin | 0.4% |
| Piperonyl butoxide | 1.0% |

Water can be added to the above mixture as required.

The formulations described in Examples 2 to 6 have viscosities in the range of 30 to 50 cP (5 % aqueous solution).

EXAMPLE 7

The following is a formulation suitable for use as a fat-free dressing.

| Component | % Concentration (w/v) |
|---|---|
| Water | 76.4 |
| Egg Yolk | 4.9 |
| HPC* | 4.9 |
| Sucrose | 3.2 |
| Vinegar (12% acetic acid) | 3.1 |
| Salt | 1.5 |
| Mustard Flour | 0.1 |
| Potassium Sorbate | 0.1 |
| Xanthan Gum | 0.1 |
| Product A | 6.0 |

*HPC is a modified starch made from waxy maize.

All the dry ingredients were mixed together in a pan and the water and vinegar were added, the mixture was then heated to 90° C. and held at this temperature for 30 seconds.

The mixture was then cooled to 20° C. and the pan and contents reweighed. Loss in weight due to evaporation was corrected for by the addition of water.

The egg yolk was added gradually to the starch paste while mixing with a high-shear mixer. Mixing was continued for 3 minutes after the last of the oil and egg had been added.

A highly acceptable dressing was obtained, which had a good shelf life when stored at 4° C. in sterile jars.

A similar formulation was made using 32.5% oil and 49.9% water in replacement for the water and Product A. A similar product was obtained, showing that the fat-free formulation according to the invention was a very acceptable dressing.

I claim:

1. A process of making a product comprised of yeast cell ghosts from the autolyzed remains of *Saccharomyces cerevisiae* yeasts in yeast refuse, said yeast refuse having a solids content not exceeding 20% by weight comprised of disrupted cell walls and unlysed whole dead cells from said *Saccharomyces cerevisiae* yeasts, said process comprising the following sequential steps:

(a) extracting said yeast refuse derived from said *Saccharomyces cerevisiae* yeasts with a food-grade alkaline salt selected from the group consisting of sodium bicarbonate, calcium bicarbonate, potassium bicarbonate, sodium carbonate, calcium carbonate and potassium carbonate, in an amount sufficient to attain a pH from 8 to 12, to obtain an extract;

(b) separating the disrupted cell walls from the unlysed whole dead cells in said extract;

(c) contacting the disrupted cell walls from said extract with an alkaline extraction agent selected from the group consisting of potassium hydroxide, sodium hydroxide and calcium hydroxide at a pH from 8 to 14 to obtain a mixture;

(d) heating the mixture to a temperature from about 65 to 85° C. for at least one hour;

(e) bleaching and oxidizing the mixture with a bleach selected from the group consisting of hydrogen peroxide and a food-grade oxidizing or reducing agent, to obtain a bleached material; and (f) lowering the pH of the bleached material to from 5 to 6 using a food-grade acid selected from the group consisting of citric acid, ortho-phosphoric acid, hydrochloric acid and sulfuric acid.

2. A process according to claim 1, wherein said alkaline salt comprises sodium bicarbonate or calcium bicarbonate.

3. A process according to claim 1 or 2, wherein said alkaline salt is in an amount of up to 2.5% by weight, based on the total volume of said refuse.

4. A process according to claim 1, wherein said yeast refuse has a solids content of 2 to 12% by weight and a viscosity in the range of 5–15 cP.

5. A process according to claim 4, wherein said bleaching is carried out using hydrogen peroxide to produce a bleached material which is pale cream or white.

6. A process according to claim 1, which further comprises the step of:

(g) contacting said bleached material with a yeast-lytic enzyme having endo-beta glucanase activity.

7. A process of making a product comprised of yeast cell ghosts from the autolyzed remains of *Saccharomyces cerevisiae* yeasts in yeast refuse, said yeast refuse having a solids content not exceeding 20% by weight comprised of disrupted cell walls and unlysed whole dead cells from said *Saccharomyces cerevisiae* yeast, said process comprising the following sequential steps:

(a) extracting said yeast refuse derived from said *Saccharomyces cerevisiae* yeast with a food-grade alkaline salt selected from the group consisting of sodium bicarbonate, calcium bicarbonate, potassium bicarbonate, sodium carbonate, calcium carbonate and potassium carbonate, in an amount of up to 2.5% by weight, based on total volume of said refuse, and sufficient to attain a pH from 8 to 12, to obtain an extract;

(b) separating the disrupted cell walls from the unlysed whole dead cells in said extract;

(c) contacting the disrupted cell walls from said extract with an alkaline extraction agent selected from the group consisting of potassium hydroxide, sodium hydroxide and calcium hydroxide at a pH from 8 to 14 to obtain a mixture;

(d) heating the mixture to a temperature from about 65 to 85° C. for at least one hour;

(e) bleaching and oxidizing the mixture with a bleach selected from the group consisting of hydrogen peroxide and ascorbic acid to obtain a bleached material; and (f) lowering the pH of the bleached material to from 5 to 6 using a food-grade acid selected from the group consisting of citric acid, ortho-phosphoric acid, hydrochloric acid and sulfuric acid.

\* \* \* \* \*